(12) United States Patent
Karpas

(10) Patent No.: US 7,387,873 B2
(45) Date of Patent: Jun. 17, 2008

(54) HUMAN MYELOMA CELL LINE

(75) Inventor: Abraham Karpas, Cambridge (GB)

(73) Assignee: Cambridge University Technical Services Ltd., Cambridge (GB)

( * ) Notice: Subject to any disclaimer, the term of this patent is extended or adjusted under 35 U.S.C. 154(b) by 789 days.

(21) Appl. No.: 10/336,424

(22) Filed: Jan. 3, 2003

(65) Prior Publication Data

US 2004/0023339 A1 Feb. 5, 2004

Related U.S. Application Data

(63) Continuation of application No. PCT/GB01/03059, filed on Jul. 9, 2001.

(60) Provisional application No. 60/270,588, filed on Feb. 23, 2001.

(30) Foreign Application Priority Data

Jul. 7, 2000 (GB) ................................ 0016824.5
Jul. 12, 2000 (GB) ................................ 0017139.7

(51) Int. Cl.
| | |
|---|---|
| *C12Q 1/00* | (2006.01) |
| *C12Q 33/53* | (2006.01) |
| *C12P 21/08* | (2006.01) |
| *C12N 5/24* | (2006.01) |
| *C12N 15/07* | (2006.01) |

(52) U.S. Cl. .................. 435/4; 435/69.6; 435/70.21; 435/372; 435/372.1; 435/372.2; 435/450; 435/451

(58) Field of Classification Search .................... None
See application file for complete search history.

(56) References Cited

U.S. PATENT DOCUMENTS

| 4,720,459 A | 1/1988 | Winkelhake | ............. 435/240.2 |
|---|---|---|---|
| 4,833,077 A | 5/1989 | Abe et al. | ..................... 435/68 |

FOREIGN PATENT DOCUMENTS

WO    WO-02/04607    7/2001

OTHER PUBLICATIONS

Kipps and Herzenberg ('Schemata for the production of monoclonal antibody-producing hybridomas', In: Applications of Immunological Methods in biomedical Sciences, vol. 4, Weir et al, Ed.s, 1986, pp. 108. 1108.9).*

Teng et al (PNAS, 1983, vol. 80, pp. 7308-7312.*

Kozbor and Croce ('Fusion Partners for Production of Human Monoclonal Antibodies', In: Human Hybridomas and Monoclonal antibodies, Engelman et al, Ed.s, 1985, pp. 21-36).*

Roos et al ('Control of membrane Fusion in Polyethylene Glycol-Resistant Mutants', In: "Cell Fusion", 1987, A Sowers, Ed., pp. 123-144).*

Glick (Fundamentals of Human Lymphoid culture, 1980, pp. 103-107).*

Schlom ('Monoclonal Antibodies: They're More and Less Than You Think', In: Molecular Basis of Oncology, Broder, Ed., 1991, pp. 95-134.*

Burnett et al ('Human Monoclonal Antibodies to Defined Antigens', Human Hybridomas and Human Monoclonal Antibodies, Engelmann et al, Ed.s, 1985, pp. 113-133).*

Banerjee et al (Hum Antibodies Hybridomas. 1990;1(1):55-63.*

Cole, S., et al., "Human monoclonal antibodies", *Molecular and Cellular Biochemistry*, 62, (1984),pp. 109-120.

Hulette, C., et al., "Production of a Human Monoclonal Antibody to HLA by Human-Human Hybridoma Technology", *AJP*, (1985),pp. 10, 12, 14.

Karpas, A., et al., "A human myeloma cell line suitable for the generation of human monoclonal antibodies", *PNAS*, 98(4), (2001),pp. 1799-1804.

Karpas, A., et al., "Human Myeloma Cell Line Carrying a Philadelphia Chromosome", *Science*, 216, (1982),pp. 997-999.

Karpas, A., et al., "Human Plasmacytoma with an unusual Karyotype Growing in Vitro and Producing Light-Chain Immunoglobulin", *The Lancet*, (1982),pp. 931-935.

O'Oka, H., et al., "Establishment of Stable Cell Lines Producing Anti-Pseudomonas aeruginosa Monoclonal Antibodies and Their Protective Effects for the Infection in Mice", *Microbiol. Immunol.*, 36(12), (1992),pp. 1305-1316.

Olsson, L., et al., "Human-human hybridomas producing monoclonal antibodies of predefined antigenic specificity", *Proc. Natl. Acad. Sci.*, 77(9), (1980),pp. 5429-5431.

Yongjun, G., et al., "Establishmnet of Human Myeloma Cell Line Km-2R and its Preliminary Application to Human-Human Hybridoma Research", *Chinese Medical Sciences Journal*, 6, (1991),pp. 92-95.

* cited by examiner

*Primary Examiner*—Karen A. Canella
(74) *Attorney, Agent, or Firm*—Morgan, Lewis & Bockius LLP

(57) ABSTRACT

There is provided a human myeloma cell tine for use in a method for producing a human monoclonal antibody.

18 Claims, 5 Drawing Sheets a)

b)

HUMAN MYELOMA CELL LINE

RELATED APPLICATIONS

This application is a continuation under 35 U.S.C. 111(a) of PCT/GB01/03059 filed Jul. 9, 2001 and published in English as WO 02/04607 A1 on Jan. 17, 2002, which claims priority from Great Britain application GB 0016824.5 filed Jul. 7, 2000, Great Britain application GB 0017139.7 filed on Jul. 12, 2000, and U.S. provisional application 60/270,588 filed Feb. 23, 2001, which applications and publication are incorporated herein by reference.

The present invention relates to a human myeloma cell line. In particular it relates to the use of a human myeloma cell line in a method for making a human hybridoma capable of producing human monoclonal antibodies.

BACKGROUND

The technique for providing murine monoclonal antibodies was devised in 1975 by Köhler & Milstein (1,2). In this method, antibody-producing spleen cells from an immunised mouse are fused with cells from a mouse myeloma to produce hybrid cells known as hybridomas. After fusion, the cells are selected using drugs that kill the myeloma parental cell, whereas the unfused parental spleen cells have a limited life-span and soon die, so that only hybrid cells survive. These hybridomas have the capacity to proliferate indefinitely and to secrete antibody specific for the antigen used to immunise the spleen cell donor. Those hybridomas producing antibody of the desired specificity are cloned, resulting in a hybridoma cell line producing a homogenous population of antibody molecules (i.e. monoclonal antibodies).

Much research effort has been directed to the adaptation of this technology to produce human monoclonal antibodies. Attempts to use the mouse myelomas to derive human monoclonal antibodies were unsuccessful because the hetero-specific hybrids quickly lose the relevant human chromosomes. Attempts have also been made to use known antibody-secreting human myeloma cell lines (such as the IgEλ secreting U266 human myeloma cell line, and the RPMI-8226 cell line which contains a heterogeneous mixture of lymphoblastoid and plasmablast cells (3)) for the production of human monoclonal antibodies, but they have all failed, in spite of promising early reports.

Due to the lack of success in obtaining human antibody-producing hybridomas, various alternative cell lines have been considered. For example, the Epstein-Barr virus (EBV) has been used to immortalise antibody-producing human peripheral blood B-lymphocytes. However, such cell lines have a number of drawbacks when compared with the murine monoclonal antibody-producing hybridomas. For example, they tend to be unstable with respect to growth, they are low producers of antibodies, and EBV does not preferentially immortalise lymphoblasts engaged in antibody responses (4).

Strategies have also been developed to produce monoclonal antibodies with human character which bypass the need for an antibody-producing human cell line. For example, useful mouse monoclonal antibodies have been "humanised" by linking rodent variable regions and human constant regions (chimeric antibodies) (13). This somewhat reduces the human anti-mouse immunogenicity of the antibody but residual immunogenicity is retained by virtue of the foreign V-region framework. Moreover, the antigen-binding specificity is essentially that of the murine donor. CDR-grafting and framework manipulation (EP 0239400) has improved and refined antibody manipulation to the point where it is possible to produce humanised murine antibodies which are acceptable for therapeutic use in humans. However, the antibody specificity remains determined by the murine binding site donor. Moreover, their production involves complex manipulation of sequences and is laborious.

Phage display technology has been developed for the in vitro generation of human monoclonal antigen-binding fragments, whose V genes can be recovered and engineered into antibody genes to produce monoclonal antibodies (14). However, production of human monoclonal antibodies by this route is a complex multi-step procedure, and the binding specificity of the antibodies, since it is engineered in vitro as a result of combination of randomly-generated sequences, is not subjected to in vivo affinity maturation as is the case with natural antibodies.

A transgenic mouse strain which contains human instead of mouse immunoglobulin genes has been developed (15). This mouse strain contains human genes and produces human antibodies; however because the diversity created is selected not in a human but the mouse host, and the antibodies undergo affinity maturation in the mouse, the antibodies are not truly human.

From an analytical perspective, none of the known methods is capable of dissecting man's immune response to specific antigen challenges. Direct analysis of genes from heavy and light chains following polymerase chain reaction (PCR) amplification has become the method of choice to characterise the type of antibodies expressed by people in certain conditions This method has the disadvantage that the information of the heavy-light chains pairing is lost.

The murine hybridoma procedure for producing monoclonal antibodies has the added advantage (over the above-mentioned non hybridoma based procedures) that it can preferentially immortalise antigen activated B cells, thus producing a long-lasting supply of monoclonal antibodies.

There is thus a need for a method for producing human monoclonal antibodies which has all the advantages of the conventional murine monoclonal antibody production method.

SUMMARY OF THE INVENTION

The present invention provides a human myeloma cell line which is capable of acting in an analogous manner to the mouse myeloma used in conventional methods for making murine monoclonal antibodies. Therefore, for the first time, the present invention enables the reliable production of truly human hybridomas and monoclonal antibodies.

The present invention thus concerns a human myeloma cell line which is capable of being fused with a human lymphocyte using a standard technique, such as a polyethylene glycol (PEG) fusion protocol, use of inactivated Sendai virus (2) or electrofusion methods (17), to produce hybrid cells. The present inventor has also developed a method for producing a myeloma cell line with a considerable growth advantage (i.e. a much shorter doubling time than a primary plasma cell culture from a myeloma patient).

The human myeloma cell line of the present invention can be used as a general antibody producing cell. For example, previously characterised antibodies can be produced by transfection of the myeloma cell line with known antibody genes. The myeloma cell line is suited for "physiological" antibody production because the post-translational modifications of proteins produced by the myeloma cells are likely to be identical to those produced by human antibody-producing cells.

In a preferred embodiment, however, the myeloma cell line of the present invention is used in a method for producing a human hybridoma which is capable of producing human monoclonal antibodies. Further aspects of the invention, therefore, relate to: a method for producing a hybridoma, which comprises the step of fusing a human myeloma cell line with a human lymphocyte; a human hybridoma cell line produced by such a method; and a human monoclonal antibody produced by such a hybridoma.

The hybridoma-production method the present invention can be used to immortalise human antibodies that are provoked by the natural body reaction in pathological conditions. This enables an immune response to be monitored over time, and also provides a source of antibodies which are more likely to be useful in therapy than antibodies prepared by other methods. Analysis of the specificity of such antibodies can be used to provide information on the disease-specific antigens which provoked the antibody in vivo. This information can, in turn be used to devise antigen-based therapeutic strategies, such as improved vaccines.

Panel:
1 Small quantity of κ light chain produced by the myeloma cells
2 IgG that react with the gp41 HIV-1 produced by the hybrid with the 164 cells.
3,4 IgG producing hybridoma formed by fusing the myeloma cells with fresh white blood cells.
5, 8, 9, 16 IgG producing hybridoma formed with tonsil cells.
6,7 Two hybridomas with tonsil cells that secrete the κ light chain only.
10-12 IgM secreted by hybridoma formed with fresh tonsil cells. Band 12 suggests that this hybridoma secretes both light chains.
13 This hybridoma appears to secrete only the two light chains since it was negative for the heavy chains G and M.
14 IgG with the two light chains produced by a hybrid between the myeloma and tonsil cells.
15. Hybridoma with tonsil cells that secrete high levels of light chain only.

Figure 1:
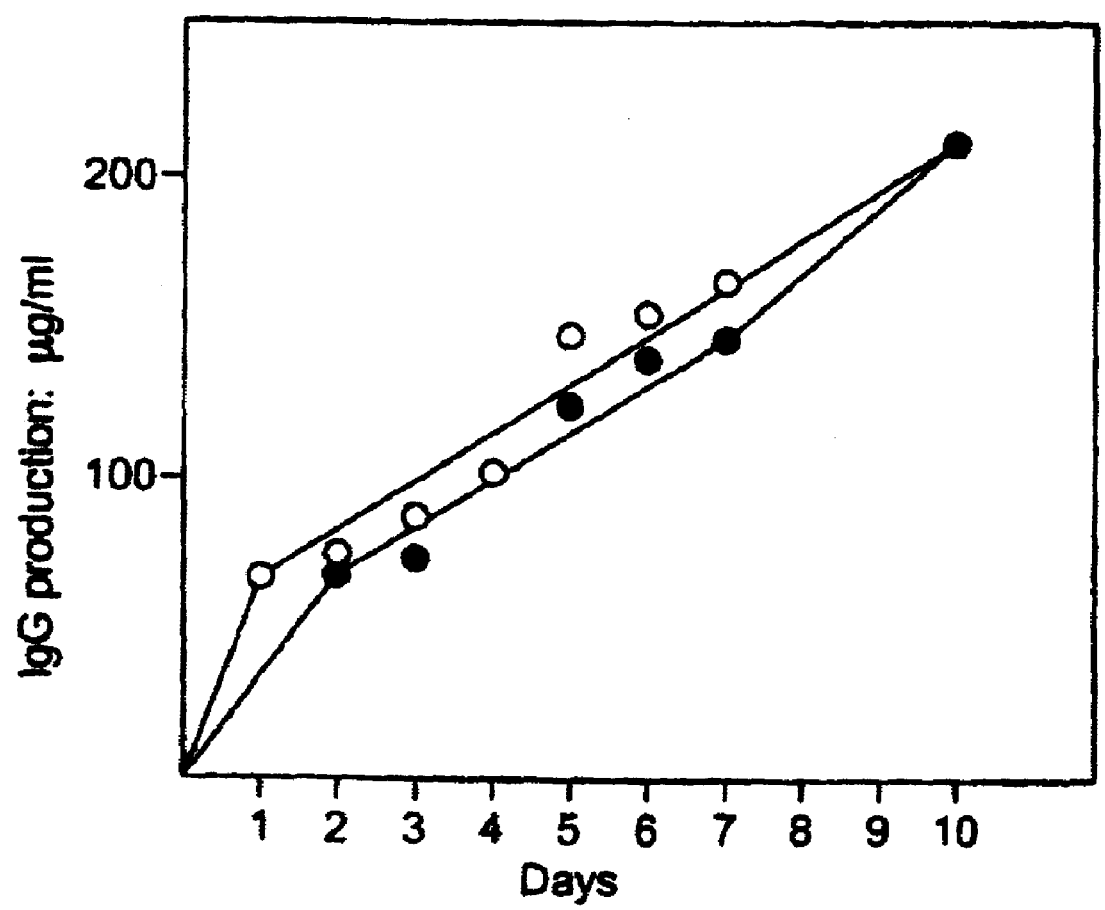
FIG. 1: Quantitation of IgG secretion by two hybridomas. 707/164(o) and 707/100(●). Each hybridoma was seeded at a concentration of $3 \times 10^5$ cells/ml in RPMI-1640 growth medium supplemented with 10% fetal bovine serum. Samples were collected at the indicated intervals for IgG quantitation by immunofixation and for cell counts. After four days the cell count of the 707/164 hybridoma reached $8 \times 10^5$ cells/ml while that of the 707/100 hybridoma was $6 \times 10^5$ cells/ml. Thereafter the number of viable cells decreased and by the $10^{th}$ day nearly all the cells were dead when the level of IgG in the medium was at its highest, namely 210 μg/ml of IgG for both cultures.
Figure 2:
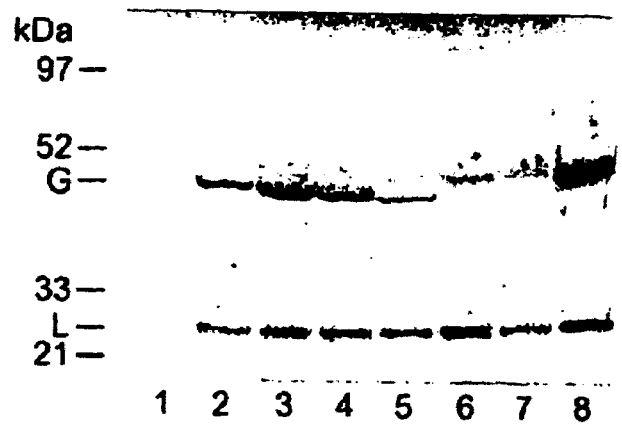
FIG. 2: Analysis of immunoglobulin secreted by the myeloma Karpas 707 cell line and hybridomas. The cells were grown at a concentration of $2 \times 10^6$ cells/ml in L-methionine, L-cystine deficient medium which was supplemented with 10% dialysed fetal bovine serum and with [$^{35}$S] methionine and cystein at 250 μCi/ml (Amersham International). The cells were incubated for 8 hours at 37° C. in a $CO_2$ incubator. After incubation the cell suspensions were centrifuged at 1000 g for 5 minutes. The supernatant was analysed by sodium dodecyl sulfate polyacrylamide gel electrophoresis after total reduction. The identity of radio-labelled secreted Ig was confirmed by immunofixation.
Figure 2:
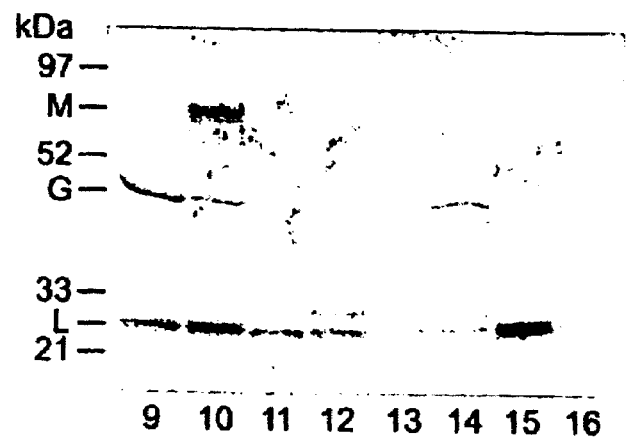
Figure 3A:
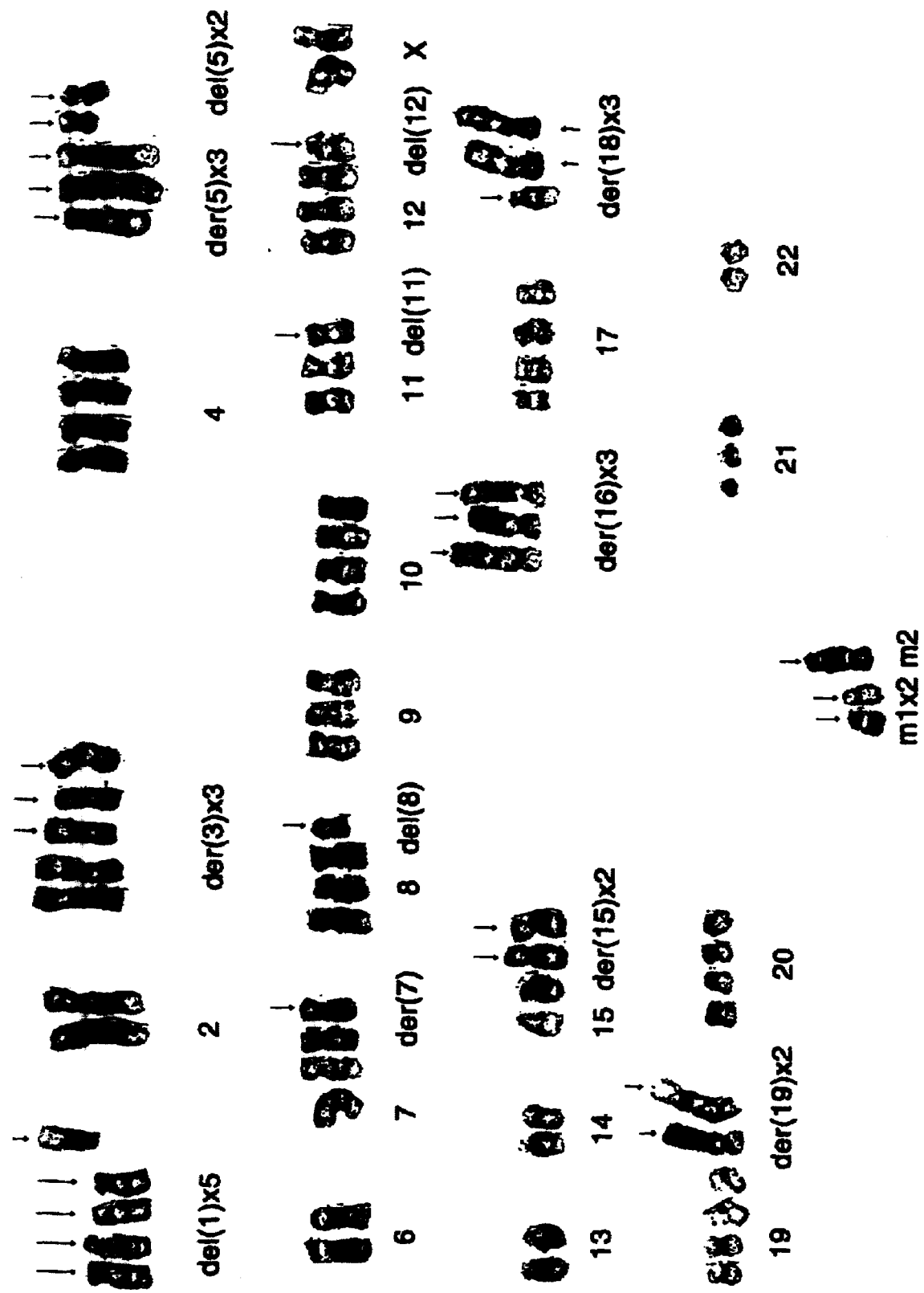
Figure 3B:
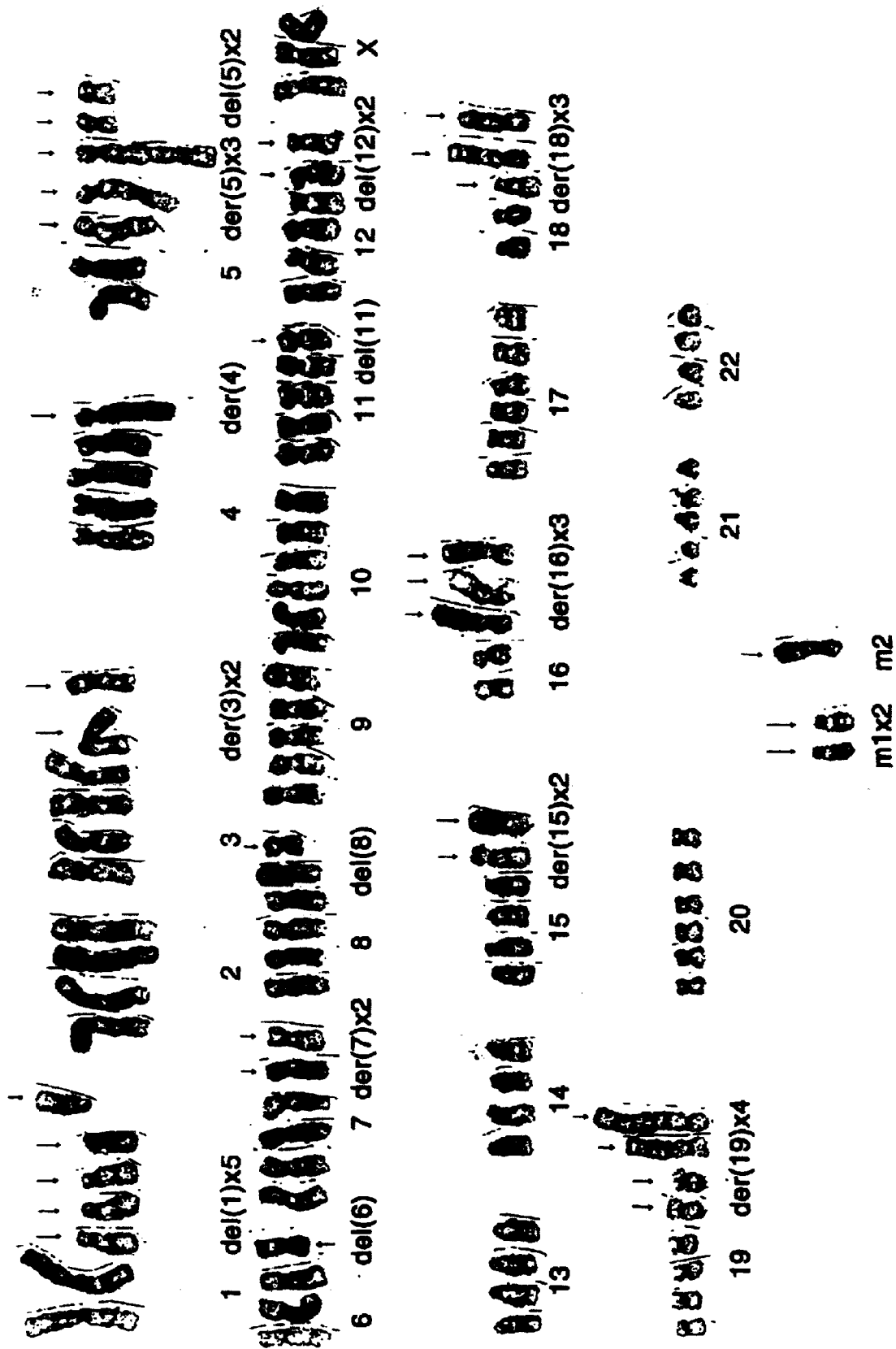

FIG. 3a Karyotype of the chromosomes of the Karpas 707 cell line which are near tetraploid. Note that chromosomes 2, 14 and 22 which contain the immunoglobulin genes are normal and diploid.
83,XX,−X,−X,del(1)(p11p36)×4,+del(1)(q11q44),−2,−2,der(3)del (3)(p21p25)inv(3) (q23q25),+del(3)(q13q21),der(5)t(1;5)(p11;q31),der(5)t(2;5)(q21;q31), del(5)(q13q33)×2,+add(5)(q31),−6,−6,add(7)(p25),del(8)(q22q24),−9, del(11)(q23q25),−11,del(12)(p12p13),−13,−13,−14,−14,add(15)(p11)×2, der(16)t(1;16)(p11;p11),add(16)(p11)×2,−16,der(18)t(1;18)(q23;p11), add(18)(p11),add(18)(q23),−18,add(19)(q13)×2,+der(19)t(1;19)(q11;p13)+der(19)t(dup(1)(q23q44);19)(q11;p13),−21,−22,−22,+mar1×2,+mar2

Karyotype of the hybridoma Karpas 707/164 which is near hexaploid containing the normal pairs of chromosomes which are readily obvious in the case of chromosomes No. 1.
125,XXX,−X,−X,del(1)(p11p36)×4,+del(1)(q11q44),−2,−2,add(3)(p25), der(3)del(3)(p21p25)inv(3)(q23q25), add(4)(q31),−4,der(5)t(1;5)(p11;q31), der(5)t(2;5)(q21;q31),del(5)(q13q33)×2,+add(5)(q31),del(6)(q21q23)−6,−6,add(7)(p25)×2,del(8)(q22q24),−9,del(11)(q23q25),−11,del(12)(p12p13)×2,−13,−13,−14,−14,add(15)(p11)×2,der(16)t(1;16)(p11;p11), add(16)(p11)×2,−16,der(18)t(1;18)(q23;p11),add(18)(p11),add(18)(q23),−18,add(19)(q13)×2,+der(19)t(1;19)(q11;p13),+der(19)t(dup(1)(q23q44);19)(q11;p13),−21,−21,−22,−22,+mar1×2,+mar2

Figure 4:
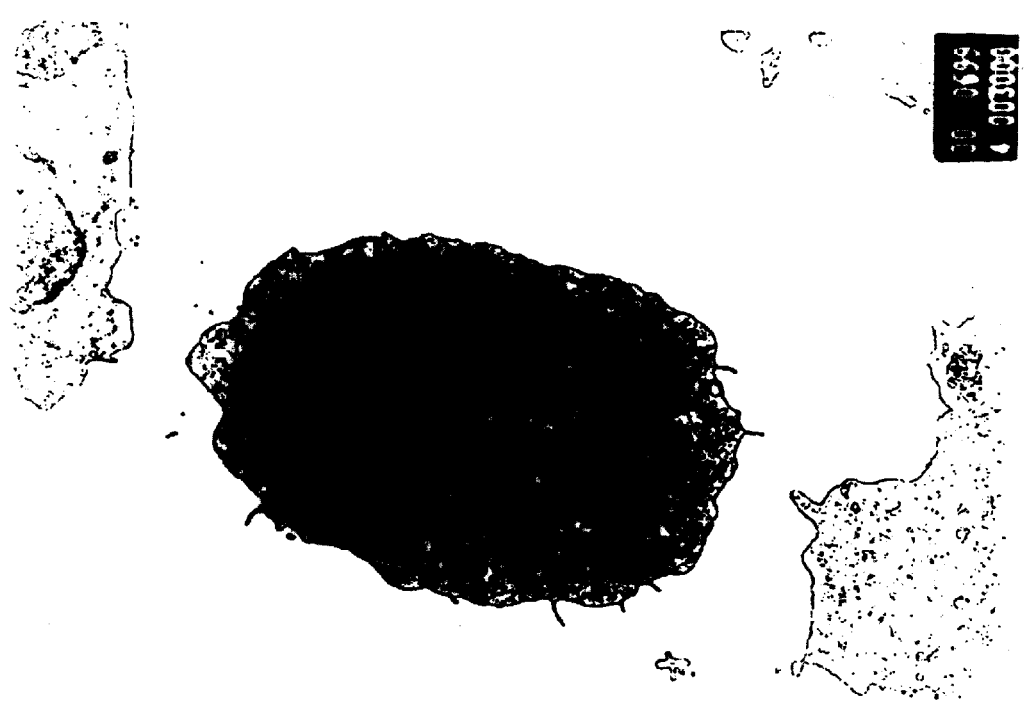
Figure 4:
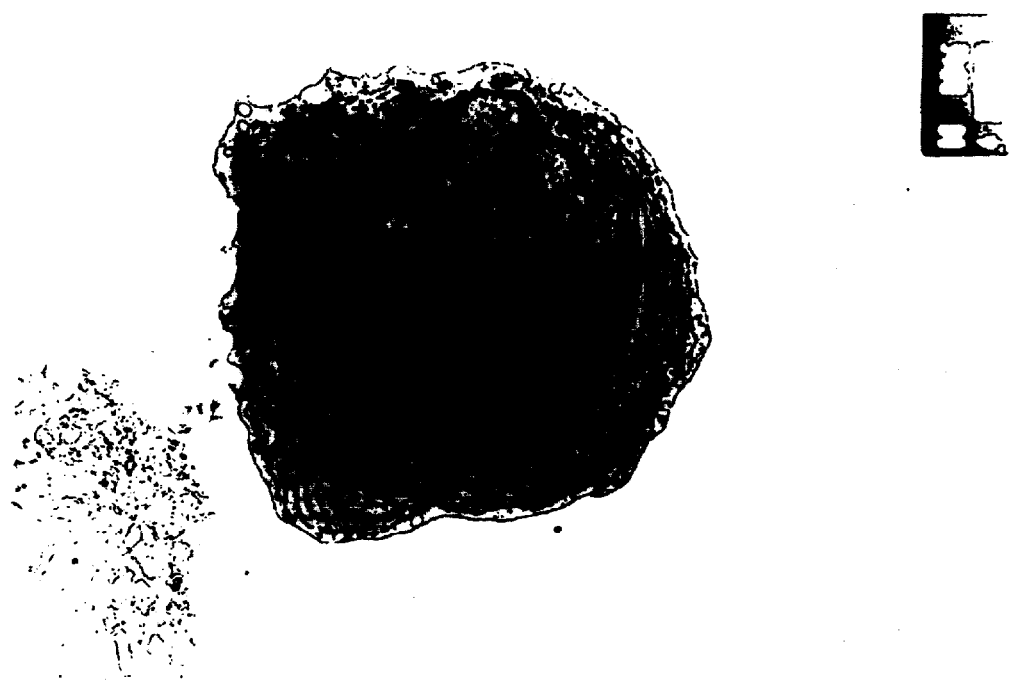

FIG. 4: Electron micrograph of the myeloma (a) and hybridoma (b). In contrast to the cytoplasm of the myeloma cells which does not appear to contain detectable levels of rough endoplasmic reticulum (RER), the cytoplasm of the hybridoma is taken up by parallel and concentric RER resembling plasma cells. These morphological observations can be correlated with the low level of κ light chain produced by the myeloma and high levels of IgG which is secreted by a hybridoma. The cells were fixed in 3% gluteraldehyde and the ultra-thin sections stained in uranyl acetate and lead citrate.

DETAILED DESCRIPTION OF INVENTION

In a first aspect, the present invention relates to a human myeloma cell line which is suitable for use in a method for producing a human monoclonal antibody-secreting hybridoma.

The myeloma cell line may be developed from primary plasma cell cultures from patients with myeloma, for example from the bone marrow or peripheral blood of such patients.

In order to develop a homogenous cell line, the cells from the patients are cultured in vitro and amplified.

It is normal for newly developed human myeloma cell lines to have a relatively long doubling time, of the order of 70 hours. However, the present inventor has surprisingly found that it is possible to produce a much faster growing cell line by culturing the cells in vitro. For example, it is possible to reduce the doubling time to approximately 35 hours or less.

The myeloma cell line of the present invention may have a doubling time which is less than 0.75, preferable less than 0.5 times the doubling time of the cell line before in vitro culture treatment. The myeloma cell line of the present invention may have a doubling time of less than 50 hours, preferably less than 40 hours, more preferably about 30 hours.

In order to use the standard polyethylene glycol (PEG) fusion protocol, the myeloma cell line of the present invention may be resistant to PEG. The present inventor found that 99% of human myeloma cells were killed after first treatment with PEG for lymphocyte fusion. Myeloma cells may be made PEG-resistant by treating cells with multiples cycles of PEG. The present inventor has found that in the region of twenty cycles of treatment produces a cell line in which only about 25% of cells are killed by PEG treatment. Selection of a PEG-resistant myeloma cell results in a cell line which can be fused with human lymphocytes to produce a human/human hybridoma in accordance with the present invention.

In the standard murine monoclonal antibody-secreting hybridoma production method, fused cells are selected using hypoxanthin, aminopterin, thymidin (HAT) medium. Murine myeloma cells are HAT-sensitive because they lack the enzyme hypoxanthine:guanosine phosphoribosyl transferase (HGPRT), whereas hybridoma cells are HAT-resistant, the HGPRT gene being provided by the spleen cell fusion partner. In order to use the same selection procedure, the myeloma cell line of the invention should be sensitive to HAT. HAT sensitivity may be selected by growth in 8-azaguanine and/or 6-thioguanine or other selective agents as known in the art. As used herein, the term "HAT-sensitive" means that, in a hybridoma fusion procedure, treatment with HAT medium results in preferential killing of unfused myelomas such that hybridoma cells may be isolated.

It is convenient for the myeloma cell line to be Ouabain resistant, to facilitate the fusion and selection procedure with cell lines or with fresh cells isolated from tissues (such as bone marrow, tonsil, lymph node, spleen and malignant tissue). Cells may be rendered Ouabain resistant by continued culture in increasing Ouabain concentrations. The resulting cell lines are HAT-sensitive and Ouabain resistant.

It has been found that the myeloma cells having a growth advantage have an increased chromosome number compared to myeloma cells with longer doubling times. The myeloma cells of the present invention may have an increase in the number of chromosomes (anuploid), or be near tetraploid, and may have a number of gross chromosomal abnormalities. However, one or more (preferably all) of chromosomes 2, 14 and 22 may be normal and/or diploid. Chromosomal analysis may be performed using standard techniques such as the G-banding method.

The present inventor has produced and characterized a human myeloma cell line which has a short doubling time, is PEG resistant, Guabain resistant and HAT sensitive (see the Examples). This cell line is known as "Karpas 707H", and a sample has been deposited at the ECACC, Salisbury, Wiltshire, SP4 OJG, United Kingdom under Deposit No. 00071108, on Jul. 11, 2000.

The second aspect of the invention relates to a method for producing a myeloma cell line. In addition to steps selecting for: a growth advantage, HAT-sensitivity, Ouabain-resistance and/or PEG sensitivity (as described above), the method may also comprise the step of introducing into the cells a marker capable of conferring sensitivity or resistance to an agent other than HAT, Ouabain and PEG. Such a marker or marker(s) may be introduced into the cell by, for example, genetic engineering methods known in the art. Representative markers: enzymes producing a detectable product, such as β-galactosidase; proteins which confer antibiotic resistance or susceptibility; and genes whose presence is fatal to the cell under certain conditions ("suicide genes"), such as herpes simplex virus thymidine kinase (HSVTK) which causes cell death in the presence of gancyclovir.

The third aspect of the invention relates to a method for producing a human hybridoma cell line. The hybridoma may be produced by a method analogous to the conventional method for producing murine hybridomas (7). For example, the myeloma cell line of the first aspect of the present invention may be fused with a human lymphocyte using, for example, a standard PEG fusion protocol, inactivated Sendai virus or electrofusion methods.

Hybrid cells may be selected from unfused cells by any of the means known in the art. For example, hybrid cells may be selected and/or isolated by cell sorting (such as by fluorescence-activated cell sorting (FACS)), using magnetic beads or using cytotoxicity. The conventional murine method for selecting hybrid cells involves growing the cell population post-fusion in a medium containing a chemical which will selectively kill myeloma cells which are not fused with lymphocytes (such as HAT). The hybrid cells may then optionally be cloned to produce a homogenous hybridoma cell line. General methods for hybridoma production are known in the art. For example, the following procedure may be used:

A single-cell suspension of human lymphocytes from an immunised individual is formed in serum free RPMI 1640, supplemented with 2 mM L-glutamine, 1 mM sodium pyruvate, 100 units/ml penicillin, and 100 μg/ml streptomycin (RPMI). The cell suspension is filtered through sterile 70-mesh Nitex cell strainer, and washed twice by centrifuging at 200 g for 5 minutes and resuspending the pellet in 20 ml serum free RPMI.

$2 \times 10^8$ lymphocytes are combined with $4 \times 10^7$ myeloma cells (kept in log phase in RPMI with 11% foetal bovine serum (FBS) for three days prior to fusion), centrifuged and the supernatant is aspirated. The cell pellet is dislodged and 2 ml of 37° C. PEG 1500 (50% in 75 mM HEPES, pH 8.0) is added while stirring over the course of one minute, followed by the addition of 14 ml of serum free RPMI over seven minutes. Additional RPMI can be added and the cells are centrifuged at 200 g for 10 minutes. After discarding the supernatant, the pellet is resuspended in 200 ml RPMI containing 15% FBS, 100 mM sodium hypoxanthine, 0.4 mM aminopterin, 16 mM thymidine (HAT), 25 units/ml IL-6 and $1.5 \times 10^6$ lymphocytes/ml. The suspension is dispensed into ten 96-well flat bottom tissue culture plates at 200 111/well. Cells are fed on days 2, 4, and 6 days post-fusion by aspirating 100 μl from each well with an 18 G needle, and adding 100 μl/well plating medium with or without 10 U/ml IL-6 and lacking lymphocytes.

When cell growth reaches 60-80% confluence, culture supernatants are taken from each well and screened for reactivity to the desired antigen by ELISA. ELISAs may be performed as follows. Immulon 4 plates are coated at 4° C. with 50 μl/well with 100 ng/well of antigen in 50 mM carbonate buffer, pH 9.6. Plates are washed with PBS with 0.05%, Tween 20 and blocked 30 minutes at 37° C. with 0.5% Fish Skin Gelatin. Plates are washed as described above and 50 μl culture supernatant is added. After incubation at 37° C. for 30 minutes, 50 μl of horseradish peroxidase conjugated goat anti-human IgG(fc) [diluted 1:10,000 in PBST] is added. Plates are incubated at 37° C. for 30 minutes, washed with PBST and 100 μl of substrate, consisting of 1 mg/ml TMB and 0.15 ml/ml 30% $H_2O_2$ in 100 mM Citrate, pH 4.5, is added. The colour reaction is stopped with the addition of 50 ml of 15% $H_2SO_4$. $A_{450}$ is read on a plate reader.

The term lymphocyte is intended to include any antibody-producing cell. For example, the lymphocyte may be a lymphoblast, such as an EBV-transformed B cell. The lymphocyte may also be an in vitro cultured cell. Alternatively, the lymphocyte may be freshly isolated from a human subject. For example, the lymphocytes can be obtained from organs such as tonsils as well as lymph nodes, spleen, blood or bone marrow.

A human subject may be a healthy individual, in particular an individual who has been immunised with a particular antigen, or who has had (and recovered from) a particular disease. The human subject may alternatively be an individual who has a particular disease. A lymphocyte from the human subject may, therefore, be capable of producing an antibody of interest.

Myelomas according to the invention may also be fused with non-antibody-producing lymphocytes, or other white blood cells, which produce lymphokines. Especially preferred are tumour-infiltrating cells which produce anti-tumor antibodies or lymphokines of therapeutic utility. The hybridomas thus obtained are capable of reliably producing anti-tumor antibodies or lymphokines in large quantities.

One advantage with the hybridoma-production method of the present invention, as well as the conventional method for producing mouse monoclonal antibody-secreting hybridomas, is that the myeloma cell line preferentially fuses with antigen-activated lymphocytes.

The present invention also provides a hybridoma cell line, and a monoclonal antibody produced by such a cell line.

Preferably the hybridoma of the present invention produces a high yield of antibodies. For example, the hybridoma may secrete more than 100 µg/ml antibody, preferably at least 200 µg/ml antibody, more preferably at least 300 µg/ml antibody.

The hybridoma of the present invention may have extensive rough endoplasmic reticulum (RER). In contrast to the cytoplasm of the myeloma cells (which do not appear to contain detectable levels of rough endoplasmic reticulum), the present inventor has found that the cytoplasm of a hybridoma cell of the present invention is taken up by parallel and concentric RER resembling plasma cells. The term "extensive" is used herein to indicate that the levels of RER in the hybridoma are comparable to those found in plasma cells.

The monoclonal antibody may be of any isotype: for example IgG, IgM, IgD, IgA or IgE. It may comprise light chains, heavy chains or both.

Preferably the antibody is useful in the prevention or treatment of a disease. For example, if a disease-specific antibody-producing cell is isolated from one patient, the cell could be immortalised by the method of the present invention, enabling the antibody to be produced in large quantities. The antibody may be given to a patient in a passive immunisation protocol to confer resistance to the disease. Alternatively, the antibody may be given to a patient suffering from the disease to boost immune responses and help clear the infection. It is possible that the derived hybridomas with various white blood cells will give rise to a range of therapeutic humoral factors.

Human monoclonal antibodies produced according to the method of the present invention may be employed in substantially any process which involves ligand-polypeptide binding, including in vivo therapeutic and prophylactic applications, in vitro and in vivo diagnostic applications, in vitro assay and reagent applications, and the like. For example, antibody molecules may be used in antibody based assay techniques, such as ELISA techniques, according to methods known to those skilled in the art.

As alluded to above, the antibodies produced according to the invention are of use in diagnostic, prophylactic and therapeutic procedures. For example, antibodies produced according to the invention are of use diagnostically in agglutination, ELISA, immunoperoxidase, Western blot and in situ protein detection by standard immunohistochemical procedures. For use in these applications, the antibodies may be labelled in accordance with techniques known to the art. In addition, such antibodies may be used preparatively in affinity chromatography procedures, when complexed to a chromatographic support, such as a resin. All such techniques are well known to one of skill in the art.

Therapeutic and prophylactic uses of antibodies prepared according to the invention involve the administration of thereof to a recipient or patient.

Substantially pure antibodies of at least 90 to 95% homogeneity are preferred for administration to a patient, and 98 to 99% or more homogeneity is most preferred for pharmaceutical uses. Once purified, partially or to homogeneity as desired, the selected antibodies may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The antibodies thereof of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the antibodies in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988)*Adv. Immunol.*, 42: 233). Arthritis is induced in a susceptible strain of mice by injection of Type II collagen (Stuart et al. (1984) *Ann. Rev. Immunol.*, 42: 233). A model by which adjuvant arthritis is induced in susceptible rats by injection of mycobacterial heat shock protein has been described (Van Eden et al. (1988) *Nature,* 331: 171). Thyroiditis is induced in mice by administration of thyroglobulin as described (Maron et al. (1980) *J. Exp. Med.,* 152: 1115). Insulin dependent diabetes mellitus (IDDM) occurs naturally or can be induced in certain strains of mice such as those described by Kanasawa et al. (1984) *Diabetologia,* 27: 113. EAE in mouse and rat serves as a model for MS in human. In this model, the demyelinating disease is induced by administration of myelin basic protein (see Paterson (1986) *Textbook of Immunopathology*, Mischer et al., eds., Grune and Stratton, N.Y., pp. 179-213; McFarlin et al. (1973) *Science,* 179: 478: and Satoh et al. (1987) *J. Immunol.,* 138: 179).

The antibodies of the present invention may also be used in combination with other antibodies, particularly human monoclonal antibodies (MAbs) reactive with other markers on human cells responsible for the diseases. For example, suitable T-cell markers can include those grouped into the so-called "Clusters of Differentiation," as named by the First International Leukocyte Differentiation Workshop (Bernhard et al. (1984) *Leukocyte Typing,* Springer Verlag, N.Y.).

Generally, the present antibodies will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition).

The antibodies of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the antibodies of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The antibodies of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present antibodies or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of antibody per kilogram of body weight, with doses of 0.05. to 2.0 mg/kg/dose being more commonly used. For prophylactic applications, compositions containing the present selected polypeptides or cocktails thereof may also be administered in similar or slightly lower dosages.

A composition containing an antibody according to the present invention may be utilised in prophylactic and therapeutic settings to aid in the alteration, inactivation, killing or removal of a select target cell population in a mammal. In addition, the antibodies described herein may be used extracorporeally or in vitro selectively to kill, deplete or otherwise effectively remove a target cell population from a heterogeneous collection of cells. Blood from a mammal may be combined extracorporeally with the selected antibodies, cell-surface receptors or binding proteins thereof whereby the undesired cells are killed or otherwise removed from the blood for return to the mammal in accordance with standard techniques.

The capacity to produce unlimited quantities of a particular antibody from an antibody-producing cell in a patient can also be used to gain valuable information about the immune response. For example, if the patient has a disease, it is possible to deduce the disease-specific antigens targeted by the immune system. This information can be used to design better drugs and vaccines to treat and/or prevent the disease.

Almost every disease produces an antibody-mediated immune response, and so is a candidate for prevention/treatment by an antibody-mediated therapy. The procedure of the present invention will be invaluable to immortalise human antibodies provoked by the natural defensive reaction of pathological conditions. Of particular interest, however, is the use of the method of the present invention to immortalise tumour-infiltrating lymphocytes. This may produce useful anti-cancer antibodies and also uncover tumour specific antigens. Such antigens could in turn be used as anti-cancer vaccines.

By analysing antibodies produced at different times, it is also possible to map the course of an immune response to antigenic challenge. This may provide valuable information on the optimum timing for a particular treatment strategy or vaccination protocol.

In a further aspect of the present invention there is provided the use of a human myeloma cell line according to the first aspect to produce an antibody, by transfection of the cell line with antibody-producing genes. The post-translational modifications effected by the human myeloma are identical to those formed in human antibodies. Thus, for biotechnological production, the human myeloma line is preferred to produce antibodies derived not only from human hybridomas but also by transfection of already known antibody genes.

A human hybridoma cell line of the present invention may also be used to select a mutant that will be also HAT-sensitive in the same way that the murine Sp2/0-Ag14 was developed to produce a hybrid hybridoma (16) following fusion with another lymphocyte. In particular, a hybridoma produced using the myeloma cell line of the present invention which produces low/undetectable levels of antibody, but has high levels of RER, may be selected for fusion with a second lymphocyte capable of producing an antibody of interest. In this way, a hybrid hybridoma may be produced which is capable of secreting high titres of the desired antibody.

The following examples serve to illustrate the present invention, but should not be construed as a limitation thereof. The invention particularly relates to the specific embodiments described in these examples.

EXAMPLES

Example 1

Production of an Improved Human Mycloma Cell Line

The present inventor has been trying to develop new human myeloma cell lines for over twenty years. The present inventor has previously described a myeloma cell line which was developed from the bone marrow and peripheral blood of a 53 year old male patient diagnosed as having multiple myeloma (5,6). Since this cell line now secretes only κ light chain it has a potential practical advantage over myeloma cell lines that also produce the heavy chain.

Selecting for Myeloma Cells having a Growth Advantage

The doubling time of this myeloma cell line after isolation was over 70 hours, but following continuous in vitro culture over many months a faster growing cell emerged with a doubling time of approximately 30-40 hours, with an increase tendency to stick to the surfaces of glass or plastic when in stationary culture. The adherent cells can be detached easily by forceful pippeting in a similar way to the mouse myeloma cells used to generate hybridomas.

Selection for HAT-Sensitivity and Ouabain-Resistance

The conventional method for making murine hybridomas relies on the fact that the unfused murine myeloma cells are sensitive to hypoxanthin, aminopterin, thymidin (HAT). In order to select for human myeloma cells which are (HAT)-sensitive, they were grown in 8-azaguanine. Azaguanine-resistant cells that grew at a concentration of 30 μg/ml were further subjected to 30 μg/ml of 2-Amino-6-mercaptopurine (6-Thioguanine). The first twenty clones that grew out were tested for their sensitivity to HAT medium. The fastest growing clone which did not seem to produce any resistance was selected for further work. In order to be able to fuse the myeloma cells also with antibody producing cell lines it was decided to select also for an Ouabain resistant subline. Growing the myeloma cells with an increasing concentration of Ouabain eventually led to the emergence of a HAT-sensitive Ouabain-resistant subline.

Example 2

Production of a Human Hybridoma

In order to optimise the conditions and screening for hybridoma formation the present inventor decided to develop (for the initial fusions) an antibody-producing human B-cell lymphocyte with known specificity. Therefore the peripheral blood lymphocytes from healthy HIV-1 infected individual were infected with EBV. From the EBV-immortalised B-cells, cells that produced monoclonal antibodies to HTV-1 gp41 were selected and cloned, and referred to as Cell line Karpas 164. The present inventor then attempted unsuccessfully to fuse the myeloma cells with the EBV-immortalised human lymphocytes using polyethylene glycol (PEG) of different molecular weights.

In order to try to investigate the reasons for the repeated failure to develop hybrids the myeloma cells alone were treated with PEG using the same procedure as that used for cell fusion. Thereafter, the cells were seeded in growth medium, but without HAT or Ouabain, and examined for viability. Examination of the PEG-treated cells revealed that the PEG was highly toxic, killing over 99% of the cells.

Development of a PEG-Resistant Sub-Line

In view of the above findings, the present inventor decided to try and develop a PEG-resistant subline. This was achieved by treating about $10^7$ myeloma cells with PEG (1500 MW) following the protocol used for murine hybridoma formation. The few viable cells which eventually grew out were treated again with PEG. He repeated such cycles of treatment more than twenty times over a period of about 18 months before a subline of the myeloma emerged where only about one quarter of the cells were killed by the PEG treatment. However, in the process HAT-resistant cells reappeared. The cells were therefore treated once more with 8-azaguanine and cloned. A clone was isolated which did not revert when grown in HAT medium. This cell line is known as the myeloma Karpas 707 cell line, a sample of which has been deposited as Deposit No. ECACC 00071108.

Fusion with EBV-Immortalised Lymphocytes

The HAT-sensitive, PEG-resistant cells were then fused with the EBV immortalised human B-lymphocytes 164 cells producing the monoclonal antibodies to gp41 using a standard PEG fusion protocol (7). The cell suspension was seeded in multi-well plastic trays. Following growth in the presence of HAT and Ouabain, clones resembling the myeloma cell line grew out. The tissue culture fluid gave strong staining of the membranes of acetone fixed HIV-1 infected Karpas 45 T-cells in the Karpas AIDS cell test for anti-viral antibodies (8).

Characterisation of the Human Monoclonal Antibody Produced by the Hybridoma

Further studies using several polypeptides of the gp41 of HIV-1 enabled us to establish that our monoclonal antibody reacted against the peptide LAVERYLKDQQLLGIWG but it failed to react against four other peptides of the gp41 of HIV-1 (results not shown). The epitope that this monoclonal antibody recognises seems not to be present in the African NDK strain of HIV-1 (9), since the antibody fails to react with NDK infected T-cells but reacts not only with the Cambridge isolate of HIV-1 (10) but also with the early French LAV isolate (11). A database search confirms that both the French (LAV) and British (CAM1) isolates of HIV-1 share the above amino acid sequence, whereas the African isolate has a lysine to arginine mutation.

Fusion with Fresh Human Lymphocytes

After the successful fusion with the 164 cell line the present inventor decided to establish whether their myeloma cells would also form antibody-producing hybridomas with fresh human lymphocytes. They fused the myeloma cells with unfractionated white blood cells (WBC) from the peripheral blood of an adult and with tonsil cells prepared from surgically removed tonsils from two children. The cell suspensions obtained after the PEG fusion were seeded in 24 and 96 wells plastic tissue culture plates and grown in RPMI-1640 medium supplemented with 20% foetal bovine serum and HAT for the first 12 days. Thereafter, growth medium alone was used and colony formation was observed during the following 2-3 weeks in approximately 25% of the wells when the myeloma cells were fused with tonsil cells and in about 10% of the wells when the myeloma cells were fused with blood WBC. Tissue culture fluid collected from wells with active cell growth was assayed by ELISA for the presence of IgG. In this method, protein-A was used on the plastic wells to capture the IgG monoclonal antibodies produced by the newly formed hybridomas. The culture fluid from over 100 of the wells contained IgG.

The present inventor has, to date, developed over 20 independent Ig secreting hybrids from fusion with peripheral blood lymphocytes and over 100 antibody producing hybrids from fusion with tonsil cells.

Example 3

Characterisation of the Human Myeloma Cell Line and Hybridomas

Morphological Analysis of the Hybridomas

The growth pattern of many of the cells that grew out was variable. When in stationary culture, myeloma cells grow in a uniform pattern of adherent cells forming an irregular mosaic which covered the plastic surface with continuous release of cells into the culture fluid. When grown in roller flasks, most cells remain in suspension as clusters of variable size. The growth of some hybrids resembled the parent myeloma cells but many others acquired a distinct morphology and growth forms. In stationary culture, some hybridomas adhered to the plastic surfaces and displayed numerous thick but short spindles, rectangular and triangular shapes. Other grew mainly in suspension as single cells or clusters.

Ultrastructural examination of the cultured myeloma revealed that in contrast to the cells which contained large amounts of rough endoplasmic reticulum (RER) during the first year in culture (5), after long-term in vitro growth the cells have lost most of the RER. However, examination of two hybridomas, 707/164 and 707/105 (formed with blood B-cells) revealed that in both cases the hybrids resembled plasma cells (FIG. 4). A large part of the cytoplasm was taken up by parallel and concentric RER while the degree of dilatation of the cisternae varied from cell to cell. The contents of the RER appeared as fine granular material which is probably immunoglobulin. A large number of mitochondria could be seen in most sections, while sections through the Golgi area revealed highly developed apparatus. Since the ultrastructural examination of EBV-immortalised 164 B-cells revealed only a small number of short and thin strands of RER it will not be unreasonable to suggest that the fused lymphoblast somehow activates the latent myeloma RER for the production of Ig.

Chromosomal Analysis of the Myeloma Cell Line

To confirm that the antibody producing cells were indeed a hybrid of myeloma and human lymphocyte, cell cultures were prepared for chromosome analysis using the G-banding method described by Czepulkowski et al. (12). Early on, the cultured myeloma cells (like the fresh patient cells) were found to be hypodiploid with 45 chromosomes containing several chromosomal abnormalities (5). However, the myeloma cells which had the selective growth advantage (after multiple cycles of in vitro culture) and which had increased PEG-resistance were revealed to be near tetraploid containing numerous and unusual high number of gross chromosomal abnormalities. In fact 13 of the 23 chromosomes were abnormal. Karyotypic analysis revealed 5 copies of chromosome 1 all of which were also shorter than usual, and 3 marker chromosomes It is interesting to note that the chromosomes 2, 14 and 22 (which contain the immunoglobulin genes) are normal and diploid.

In order to establish whether the repeated cycles of PEG treatment induced these chromosomal karyotype abnormalities, the chromosomes of cells which were frozen prior to the PEG treatment were also analysed. The analysis revealed that all these changes were present before the PEG treatment. Hence it appears that, during the continuous in vitro culture over many months and treatment with 8-azaguanine, 6-thioguanine, HAT and Ouabain, a near tetraploid cell line emerged which had a growth advantage over the hypodiploid myeloma cells.

Chromosomal Analysis of the Hybridoma Cell Lines

Karyotype analysis of the hybridoma with the 164 cells revealed that the cells are near hexaploid, containing the near tetraploid chromosome of the myeloma cell and the normal chromosome from the lymphoblast.

Karyotype analysis of the EBV-transformed lymphoblasts (Karpas 164 line) that produce monoclonal antibody to gp41 of HIV-1 shows that about 10% of the cells display a similar translocation, t(1;16) (p11;q10) to that detected also in the myeloma cell line. This may be due to prolonged in vitro culture.

Analysis of IgG Production

As to the quantity of IgG production, a comparative assay for the secretion of antibodies to the gp41 of HIV-1 by the EBV infected lymphoblasts and the hybrid (707/164) revealed that the hybridoma produced at least eight times more antibodies than the lymphoblasts following culture of identical number of cells ($10^6$/ml) under the same conditions: Specifically, the hybrid 707/1 64 secreted 470 µg/ml of IgG while the 164 cells secreted less than the assay detection level, which is 70 µg/ml after four days in culture. Since both cell cultures have the same genetic information for the antibody synthesis it is clear that the hybridoma cells of the present invention are far more effective in antibody production.

Tests for the secretion of immunoglobulin confirm that the myeloma cells produced only a small quantity of light chain. The fusions with the tonsil cells and blood lymphocytes produced clones that secreted IgG as well as IgM. One of the hybrids which was formed with tonsil cells produces only light chains (λ+κ). Such diversity of Ig production suggests that the myeloma cell line is capable of forming hybridomas with most if not all the range of antibody producing cells. In fact the present inventor has found that the hybridomas that are formed with the myeloma cell line described herein are far more effective in antibody production than murine hybridomas (specifically, the hybridoma that secreted antibodies against gp41 of HIV-1 produced 470 µg/ml yield of IgG, and the hybridomas that were formed following fusion with blood lymphocytes produced 210 µg/ml and 150 µg/ml of IgG). It correlates with extensive rough endoplasmic reticulum (RER) which is present in the human hybridoma as compared to the sparse RER of the murine hybridoma.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention. All publications mentioned in the specification are herein incorporated by reference.

BIBLIOGRAPHY

1. Cotton, R. G. H. and Milstein, C. *Nature* 244, 42-43 (1973).
2. Kölier, G. and Milstein, C. *Nature* 256, 495-497 (1975).
3. Nilsson, K. Int. J. *Cancer* 7, 380-396 (1971).
4. Roder, J. C., Cole, S. P. C. and Kozbor, D. *Meth Enzym.* 121, 140-167 (1989).
5. Karpas, A., Fischer, P., Swirsky, D. *Science* 216, 997-999 (1982).
6. Karpas, A., Fischer, P., Swirsky, D. *Lancet* i, 931-933 (1982).
7. Galfre, G. & Milstein, C. *Meth. Enzymology*, 7B, 346 (1981)
8 Karpas, A., Gilson, W., Bevan, P. C., Oates, J. K. *Lancet* ii, 695-697 (1985).
9. Ellrodt, A. et al. *Lancet* i. 1383-1385 (1984)
10. Karpas, A. *Mole. Biol. Med.* 1, 457-459 (1983).
11. Barré-Sinoussi, F. et al. *Science* 220, 868-871 (1983).
12. Czepulkowski, B. H., Bhatt, B., Rooney, D. E. in Human cytogenetics: A practical approach. Vol 2, IRL Press, Oxford University Press (1992).
13. Winter, G. and Milstein, C. *Nature* 349, 293-299 (1991).
14. Winter, G., Griffiths, A. D., Hawkins, R. E. and Hoogenboom, H. R. *Annu. Rev. Immunol.* 12, 433-455 (1994).
15. Bruggemann, M. and Neuberger, M. S. *Immunol. Today* 17, 391-397 (1996).
16. Shulman et al. *Nature* 276, 269-270 (1978).
17. Panova & Gustafsson, (1995) Hybridoma 14,3, 265-269

The invention claimed is:

1. A human myeloma cell line which is PEG resistant and possesses one or more properties selected from the group consisting of
    a) HAT-sensitivity; and
    b) Ouabain resistance, wherein the cell line is the Karpas-707 cell line deposited in Deposit No. ECACC 00071108.

2. A method for production of a human hybridoma, which comprises the step of fusion of the human myeloma cell line of claim 1 with a human white blood cell.

3. The method of claim 2, comprising the steps of:
    a) incubating the myeloma cell line of claim 1 with a human white blood cell, in the presence of polyethylene glycol (PEG), inactivated Sendai virus, or under electrofusion conditions;
    b) selecting for hybrid cells.

4. The method of claim 3, wherein step b) comprises
    i) continuing the incubation in the presence of HAT with or without Ouabain;
    ii) selecting HAT-resistant, optionally Ouabain-resistant cells; and
    iii) culturing the HAT-resistant, optionally Ouabain-resistant cells and selecting individual hybridoma clones.

5. The method of claim 2, wherein the white blood cell is an antibody-producing lymphocyte, a lymphoblast such as an EBV-immortalised lymphocyte, or a lymphokine-producing white blood cell.

6. The method of claim 2, wherein the white blood cell is freshly isolated from a human subject.

7. The method of claim 2, wherein the human white blood cell is part of a population of lymphocytes showing varying degrees of antigen activation, and the human myeloma cell line preferentially fuses with antigen activated lymphocytes from the population.

8. A human hybridoma cell line produced by the method of claim 2.

9. The human hybridoma cell line of claim 8, having extensive rough endoplasmic reticulum.

10. A method of producing an antibody, which comprises the following steps:
    (i) isolation of a lymphocyte from a human subject;
    (ii) production of a human hybridoma by fusing the human myeloma cell line of claim 1 with the isolated lymphocyte; and
    (iii) isolation of an antibody secreted by the hybridoma.

11. A method according to claim 10, wherein the antibody is capable of treating a disease.

12. A method according to claim 11, wherein the lymphocyte is a tumor-infiltrating lymphocyte, and the antibody is useful in the treatment of cancer.

13. A method for identifying a disease-specific antigen which comprises the following steps:
    (i) production of a disease-specific antibody by the method of claim 11; and
    (ii) deduction of the antigen which is specifically recognized by the antibody.

14. A method of monitoring an immune response in a human which comprises the following steps:
    (i) isolation of lymphocytes from a human subject at varying stages of the immune response;
    (ii) production of a human hybridoma by using the lymphocytes in the method of claim 2;
    (iii) isolation of an antibody secreted by each hybridoma.

15. A method for producing a human antibody which comprises the following steps:
    (i) transfection of the human myeloma cell line of claim 1 with one or more antibody encoding gene(s);
    (ii) production of the antibody by the transfected myeloma cell line.

16. A method for producing a humoral factor, which comprises the step of fusing a cell from the myeloma cell line of claim 1 with a white blood cell which is capable of producing the humoral factor.

17. A method for selecting a mutant hybridoma, comprising selecting a mutant of the human hybridoma cell line of claim 8 useful to prepare a hybrid hybridoma.

18. A method of monitoring an immune response in a human which comprises the following steps:
    (i) isolation of lymphocytes from a human subject at varying stages of the immune response;
    (ii) production of a human hybridoma by fusing the human myeloma cell line of claim 1 with the isolated lymphocyte;
    (iii) isolation of an antibody secreted by each hybridoma; and
    (iv) analysing or comparing the quantity, specificity or type of antibody produced at the various stages of the immune response.

* * * * *